United States Patent
Pfeifer

(10) Patent No.: US 6,862,138 B2
(45) Date of Patent: Mar. 1, 2005

(54) HOLDER FOR POSITIONING A SPECIMEN SLIDE, AND APPARATUS FOR LASER CUTTING OF SPECIMENS, AND MICROSCOPE

(75) Inventor: Gerhard Pfeifer, Solms (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 0 days.

(21) Appl. No.: 10/056,584

(22) Filed: Jan. 24, 2002

(65) Prior Publication Data

US 2002/0101654 A1 Aug. 1, 2002

(30) Foreign Application Priority Data

Jan. 26, 2001 (DE) .......................... 101 03 707

(51) Int. Cl.[7] .............................................. G02B 21/26
(52) U.S. Cl. ...................... 359/391; 359/368; 359/392; 359/393; 359/394
(58) Field of Search ................ 359/368, 391, 359/392, 393, 394

(56) References Cited

U.S. PATENT DOCUMENTS

| | | | | |
|---|---|---|---|---|
| 3,572,889 A | * | 3/1971 | Bloomfield | ................. 359/390 |
| 4,248,498 A | * | 2/1981 | Georges | ...................... 359/393 |
| 4,367,915 A | * | 1/1983 | Georges | ...................... 359/385 |
| 5,795,295 A | * | 8/1998 | Hellmuth et al. | ........... 600/407 |

FOREIGN PATENT DOCUMENTS

| | | |
|---|---|---|
| DE | 8107774 | 9/1984 |
| DE | 19616216 | 10/1997 |

* cited by examiner

Primary Examiner—Drew A. Dunn
Assistant Examiner—Joshua L Pritchett
(74) Attorney, Agent, or Firm—Davidson, Davidson & Kappel, LLC

(57) ABSTRACT

The invention concerns a holder (1) for positioning a specimen slide (2) on a microscope stage (7), having a baseplate (3), retainable on the microscope stage (7), in which is configured, for reception of the specimen slide (2), an opening (3a) comprising flat support surfaces (3b) and at least one abutment surface (3c), extending substantially perpendicular to the support surface (3b), for the specimen slide (2); and having at least one spring element (4) with which, by means of a compressive force (F) acting substantially horizontally, the specimen slide (2) arranged in the opening (3a) of the baseplate (3) can be pressed against the at least one abutment surface (3c) of the opening (3a).

8 Claims, 4 Drawing Sheets

HOLDER FOR POSITIONING A SPECIMEN SLIDE, AND APPARATUS FOR LASER CUTTING OF SPECIMENS, AND MICROSCOPE

CROSS REFERENCE TO RELATED APPLICATIONS

This invention claims priority of the German patent application 101 03 707.4-42 which is incorporated by reference herein.

FIELD OF THE INVENTION

The invention concerns a holder for positioning a specimen slide on a microscope stage.

The invention furthermore concerns an apparatus for laser cutting of specimens and a microscope comprising said apparatus.

BACKGROUND OF THE INVENTION

A variety of embodiments of holders for positioning a specimen slide on a microscope stage are known from practical use. In the simplest embodiment, the specimen slide is held by two spring clamps, arranged on the microscope stage, which clamp the specimen slide between their spring limbs and the surface of the microscope stage. In addition to the fact that this type of immobilization does not make possible exact and reproducible positioning of the specimen slide with respect to the optical axis of the microscope, a disadvantage of this holder is that the spring clamps are arranged on the upper side of the microscope stage, so that collisions with the objectives of the microscope can occur.

In order to implement a holder of planar configuration, it is known from practical use to equip the holder with a baseplate, retainable on the microscope stage, in which is configured, for reception of the specimen slide, an opening comprising flat support surfaces and at least one abutment surface, extending substantially perpendicular to the support surface, for the specimen slide, the specimen slide arranged in the opening being acted upon via at least one spring element with a substantially horizontal compressive force and being pressed against the abutment surface of the opening. In this known holder, the support surfaces and abutment surfaces in the baseplate are produced by milling with a cylindrical milling cutter. Because of the cutting geometry of a cylindrical milling cutter, however, it is not possible to create an exactly perpendicular transition from the support surface to the abutment surface. Instead, there always remains in the transition region an angled flattened area on which the specimen slide comes to rest. In this position within the opening, the compressive force of the spring element can cause the specimen slide to slip or even to be pushed out of the opening. The risk of slippage of the specimen slide is further increased by the fact that the lateral edges of the specimen slide, produced by breakage, are not of exactly perpendicular configuration.

SUMMARY OF THE INVENTION

Proceeding therefrom, it is the object of the invention to configure a holder of the kind cited initially in such a way that it makes possible secure retention and reproducible positioning of the specimen slide.

The above object is achieved by a holder for positioning a specimen slide on a microscope stage, comprising:

- a baseplate, retainable on the microscope stage, in which is configured, for reception of the specimen slide, an opening with a rim,
- flat support surfaces and at least one abutment surface, extending substantially perpendicular to the support surface, for the specimen slide are form at the rim, and
- at least one spring element with which the specimen slide arranged in the opening of the baseplate is pressed against the at least one abutment surface of the opening, wherein the at least one abutment surface of the opening is configured in such a way that it exerts, on the specimen slide that is pressed against the abutment surface, a force component directed substantially downward onto the support surface of the opening.

A further object of the invention consists in making available an apparatus, equipped with such a holder, for laser cutting of specimens.

The above object is achieved by an apparatus for laser cutting of specimens, comprising:

- an X-Y microscope stage defining a stage surface;
- a holder, arranged above the stage surface of said X-Y microscope stage and being positionable in X and Y directions, for positioning a specimen slide,
- an opening for the specimen slide is formed in a baseplate of the holder, wherein the opening is configured with support surfaces and abutment surfaces for the specimen slide,
- a spring element is mounted on the specimen slide for pressing the specimen slide against the abutment surface of the opening so that the a specimen on the specimen slide is located opposite the stage surface; and
- a collection device having at least one container for collecting a specimen that has been cut out, wherein the collection device being conveyable to an open working space configured between the holder and the stage surface.

An additional object of the invention is to provide a microscope equipped with a holder, wherein the microscope as a whole allows secure retention and reproducible positioning of the specimen slide.

The above object is achieved by a microscope comprising:

- an apparatus for laser cutting of specimens,
- an X-Y microscope stage and a holder, wherein the holder is arranged above a stage surface of said X-Y microscope stage and is adjustable in X and Y directions, for positioning a specimen slide,
- a baseplate being part of the holder and the specimen slide being arranged in an opening formed in the baseplate, wherein the opening has support surfaces and abutment surfaces for the specimen slide,
- a spring element mounted on the base plate, so that a specimen arranged on the specimen slide is pressed by way of against the abutment surface of the opening and the specimen itself is located opposite the stage surface; and
- a collection device, having at least one container for collecting a specimen that has been cut out wherein the collection device being conveyable to an open working space configured between the holder and the stage surface.

Because of the fact that with the holder according to the present invention the horizontal compressive force of the spring element is divided, as a result of the configuration of the abutment surface, in such a way that the latter exerts on the specimen slide a force component directed substantially onto the support surface of the opening, the surface pressure is increased; as a result, the specimen slide is held securely and nondisplaceably in the defined position.

In order to ensure that the horizontal compressive force cannot exert any tilting motion on the specimen slide which pushes the latter out of the opening of the baseplate, it is proposed that at least one abutment surface of the opening be configured in such a way that the side of the specimen slide resting against it makes contact only in a region spaced away from the support surface and arranged above the horizontal center line of the specimen slide.

According to a practical embodiment of the invention, it is proposed that an undercut which cuts away the contact region with the specimen slide be configured in the abutment surface in the transition region from the support surface to the abutment surface. Creating the undercut represents a manner of configuring the at least one abutment surface of the opening according to the present invention that is economical and can be implemented in very simple practical terms.

In order to produce the undercut in the at least one abutment surface of the opening, it is proposed that it be generated by milling by means of a conical milling cutter or by drilling.

In order to achieve the object in terms of apparatus, the apparatus for laser cutting of specimens comprises an X-Y microscope stage; a holder according to the present invention, arranged above the stage surface of said X-Y microscope stage and adjustable in the X and Y directions, for positioning a specimen slide, the specimen slide being arranged in an opening, comprising support surfaces and abutment surfaces for the specimen slide, in a baseplate of the holder in such a way that the specimen mounted on the specimen slide that is pressed by way of a spring element against the abutment surface of the opening is located opposite the stage surface; and a collection apparatus having at least one container for collecting a specimen that has been cut out, the collection apparatus being conveyable to an open working space configured between the holder and the stage surface.

Lastly, the invention proposes a microscope that comprises an apparatus according to the present invention for laser cutting of specimens as well as a holder according to the present invention for positioning a specimen slide.

BRIEF DESCRIPTION OF THE DRAWINGS

Further features and advantages of the invention are evident from the accompanying drawings, in which the configuration of an embodiment of a holder according to the present invention for positioning a specimen slide, and of an apparatus for laser cutting of specimens, is depicted in merely exemplary and schematic fashion. In the drawings.

DETAILED DESCRIPTION OF THE INVENTION

Figure 1:
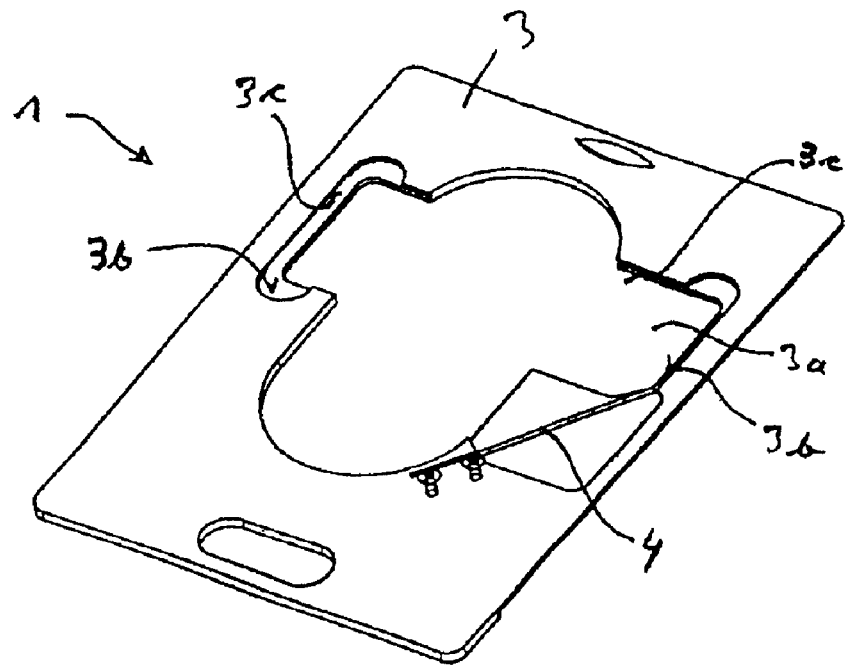
FIG. 1 is a perspective view of the baseplate of a holder according to the present invention.
Figure 2:
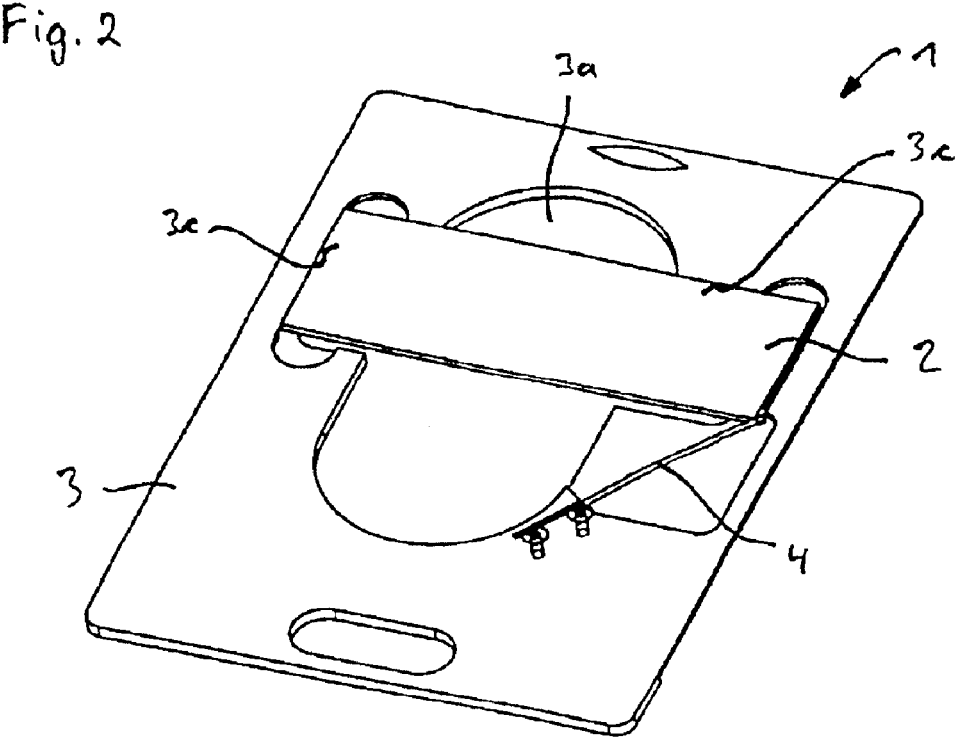
FIG. 2 is a view corresponding to FIG. 1 but with a specimen slide set into the opening of the baseplate.

FIGS. 1 and 2 are perspective views of a holder 1 for positioning a specimen slide 2, a specimen slide 2 being depicted only in FIG. 2. The holder substantially comprises a baseplate 3 in which an opening 3a for receiving specimen slide 2 is shaped, as is evident from FIG. 2. Opening 3a in baseplate 3 is shaped in such a way that it comprises flat support surfaces 3b and at least one abutment surface 3c, extending substantially perpendicular to support surface 3b, for specimen slide 2 inserted into opening 3a, as is evident from FIGS. 3 and 4.

Figure 4:
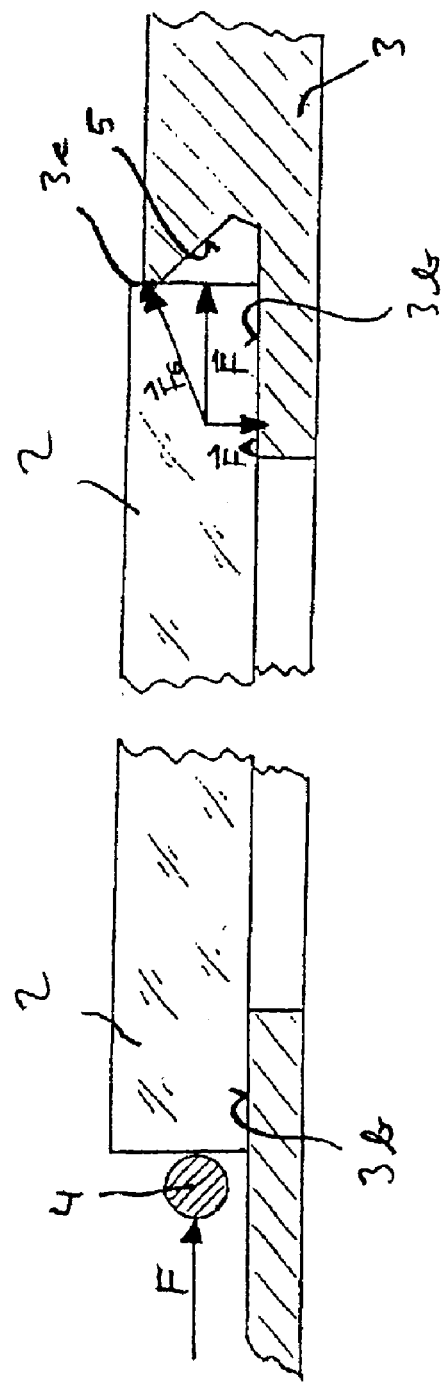
FIG. 4 is a partial, schematic, sectioned side view of a holder according to the present invention.
Figure 3:
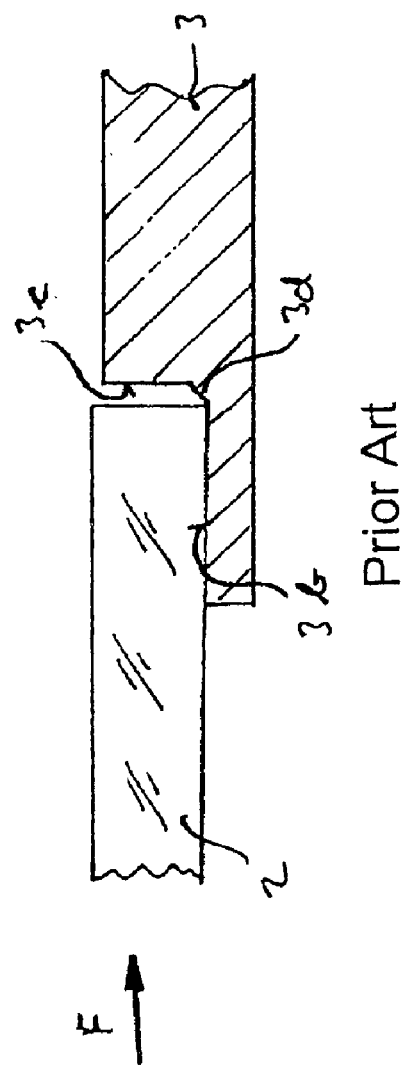
FIG. 3 is a partial, schematic, sectioned side view of a holder according to the existing art.

In order to retain specimen slide 2 securely and in accurately positioned fashion in opening 3a of baseplate 3, holder 1 furthermore comprises a spring element 4 with which a substantially horizontally acting compressive force F is exerted on specimen slide 2, as FIGS. 3 and 4 show. With this compressive force F, specimen slide 2 is pressed against the at least one abutment surface 3c of opening 3a.

FIG. 3 shows a portion of the configuration of a holder 1 according to the existing art for positioning specimen slide 2. Opening 3a in baseplate 3 of holder 1 is shaped in such a way that it forms a support surface 3b and an abutment surface 3c for specimen slide 2 inserted into opening 3a. Because opening 3a is shaped with a cylindrical milling cutter, there is formed in the transition region from support surface 3b to abutment surface 3c a bevel 3d against which, as is visible in FIG. 1, specimen slide 2 inserted into opening 3a abuts.

When a horizontal compressive force F is then exerted, via spring element 4 that is not depicted in this Figure (see FIGS. 2 through 6), on specimen slide 2 in the direction of abutment surface 3c, said compressive force F can cause specimen slide 2 to be slid along bevel 3d or even to be pushed out of opening 3a. Secure and reproducible positioning of specimen slide 2 is thus not ensured with this holder 1.

FIG. 4, on the other hand, shows a holder 1 in which, because of the configuration of abutment surface 3c of opening 3a, the horizontal compressive force F of spring element 4 is broken down into different force components $F_S$ and $F_A$; force component $F_A$ directed downward onto support surface 3b is of particular importance, since because of it, specimen slide 2 is pressed into opening 3a with increased surface pressure and in positionally accurate fashion.

In the embodiment of abutment surface 3c of opening 3a depicted in FIG. 4, an undercut 5 is configured in abutment surface 3c, in the transition region from support surface 3b to abutment surface 3c, in such a way that only a narrow contact region exists between specimen slide 2 and abutment surface 3c. To ensure that this contact region always generates on specimen slide 2 a force component $F_A$ directed toward contact surface 3b, said contact surface must act on specimen slide 2 above the horizontal center line of specimen slide 2.

Figure 5:
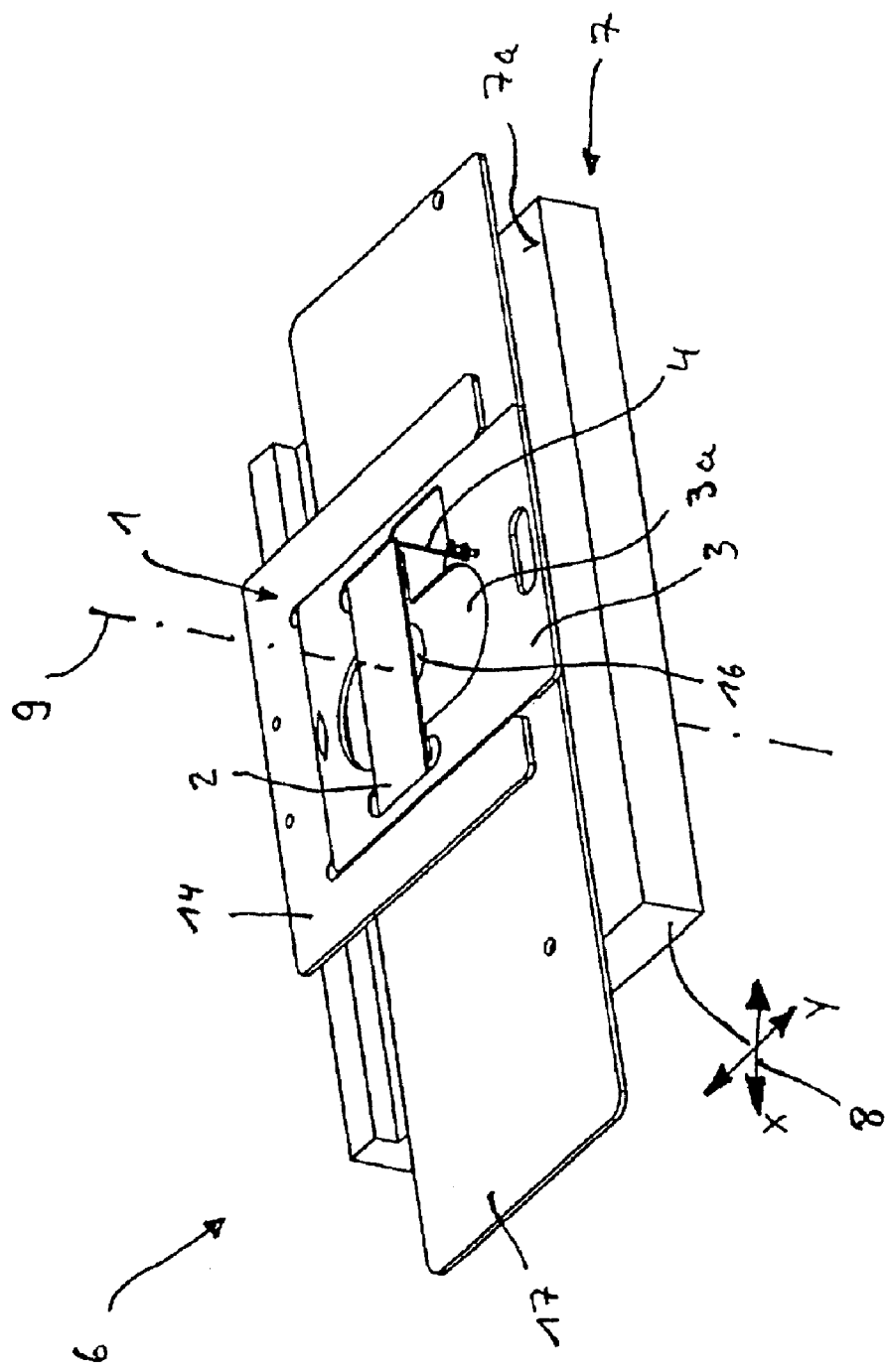
FIG. 5 is a perspective front view of an apparatus according to the present invention for laser cutting of specimens.
Figure 6:
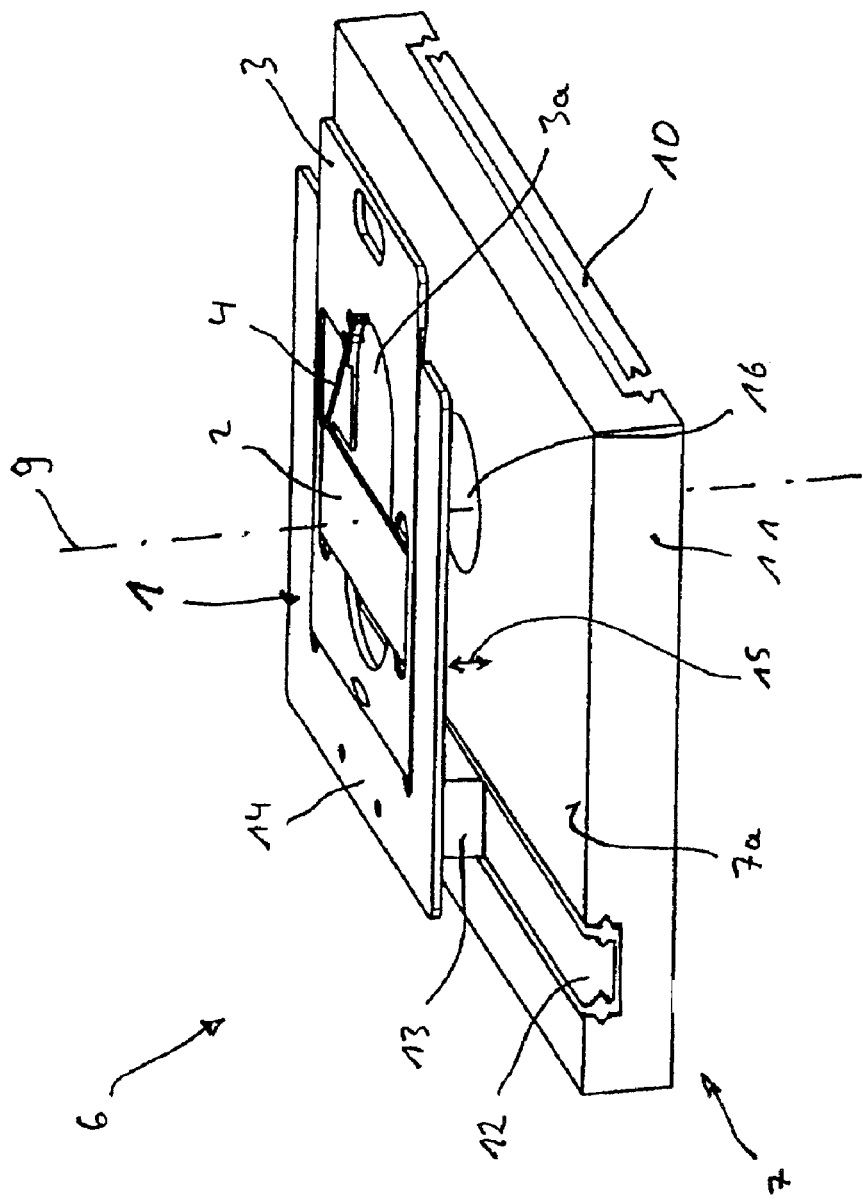
FIG. 6 is a perspective side view of the apparatus of FIG. 5.

FIGS. 5 and 6 show an apparatus 6 for laser cutting of specimens. The apparatus comprises an X-Y microscope stage 7 that can be mounted on a conventional microscope (not depicted). X-Y microscope stage 7 can be displaced, in manual or motorized fashion, in the X and Y directions depicted by the crossed double arrow 8. The microscope, operated in particular as a transmitted-light microscope, defines an optical axis 9 that is depicted in FIGS. 5 and 6 with a dot-dash line.

As is evident in particular from FIG. 6, microscope stage 7 comprises a stationary baseplate 10 on which a plate 11, displaceable in the Y direction in the exemplary embodiment depicted, is arranged. A linear guidance system 12 displaceable in the X direction is in turn arranged on displaceable plate 11. Mounted on linear guidance system 12 is a spacer 13 that in turn carries a support frame 14 for receiving a holder 1 as shown in FIGS. 1, 2, and 4 for positioning a specimen slide 2. By means of spacer 13, holder 1 is spaced away from a stage surface 7a of X-Y microscope stage 7 in such a way that an open working space 15 is configured between holder 1 and stage surface 7a.

For use on a transmitted-light microscope, there is configured in X-Y microscope stage 7 an opening 16 that is arranged with respect to the microscope in such a way that optical axis 9 extends through said opening 16. Opening 3a in baseplate 3 of holder 1, and the open space of support frame 14 serving to receive holder 1, are also aligned with respect to one another and to the microscope in such a way that they lie in optical axis 9.

For utilization of apparatus 6 for laser cutting of specimens, a collection apparatus (not depicted), which comprises at least one container and serves to collect the specimen piece that has been cut out by means of a laser beam from the specimen arranged on specimen slide 2, can be conveyed to open working space 15 below specimen slide 2. For this purpose, it is necessary for the specimen arranged on specimen slide 2 to be arranged on the side of specimen slide 2 facing toward stage surface 7a.

In FIG. 5, an additional so-called contamination shielding plate 17 is arranged between holder 1 and stage surface 7a. Contamination shielding plate 17 is intended to prevent contaminants from getting into the containers which serve to collect the cut-out specimen pieces. For that purpose, contamination shielding plate 17 seals off all containers that are not currently needed for collecting a specimen piece.

The use of the specially configured holder 1 for positioning specimen slide 2 makes it possible for the first time to ensure that specimen slide 2 can be arranged nondisplaceably, reproducibly, and in accurately positioned fashion in optical axis 9 on X-Y microscope stage 7.

What is claimed is:

1. A holder for positioning a specimen slide on a microscope stage, comprising:
   a baseplate, retainable on the microscope stage, in which is configured, for reception of the specimen slide, an opening with a rim,
   flat support surfaces and at least one abutment surface, extending substantially perpendicular to the support surface, for the specimen slide are disposed at the rim, and
   at least one spring element with which the specimen slide arranged in the opening of the baseplate is pressed against the at least one abutment surface of the opening,
   wherein the at least one abutment surface includes an undercut portion and contacts, above the undercut portion, the specimen slide in a region below an upper edge of the specimen slide and higher than a point of contact of the spring element with the specimen slide.

2. The holder as defined in claim 1, wherein the at least one abutment surface of the opening is configured in such a way that the side of the specimen slide resting against it makes contact only in a region spaced away from the support surface and arranged above the horizontal center line of the specimen slide.

3. The holder as defined in claim 1, wherein an undercut which cuts away the contact region with the specimen slide is configured in the abutment surface in the transition region from the support surface to the abutment surface.

4. The holder as defined in claim 3, wherein the undercut can be produced by milling, in particular using a conical milling cutter.

5. The holder as defined in claim 3, wherein the undercut can be produced by drilling.

6. An apparatus for laser cutting of specimens, comprising:
   an X-Y microscope stage defining a stage surface;
   a holder, arranged above the stage surface of said X-Y microscope stage and being positionable in X and Y directions, for positioning a specimen slide,
   an opening for the specimen slide is formed in a baseplate of the holder, wherein the opening is configured with support surfaces and abutment surfaces for the specimen slide,
   a spring element for pressing the specimen slide against at least a first of the abutment surfaces so that a specimen on the specimen slide is located opposite the stage surface, and
   a collection device having at least one container for collecting a specimen that has been cut out, wherein the collection device being conveyable to an open working space configured between the holder and the stage surface,
   wherein the first abutment surface includes an undercut portion and contacts, above the undercut portion, the specimen slide in a region below an upper edge of the specimen slide and higher than a point of contact of the spring element with the specimen slide.

7. A microscope comprising:
   an apparatus for laser cutting of specimens,
   an X-Y microscope stage and a holder, wherein the holder is arranged above a stage surface of said X-Y microscope stage and is adjustable in X and Y directions, for positioning a specimen slide,
   a baseplate being part of the holder and the specimen slide being arranged in an opening formed in the baseplate, wherein the opening has support surfaces and abutment surfaces far the specimen slide,
   a spring element mounted on the base plate, so that a specimen arranged on the specimen slide is pressed against at least a first of the abutment surfaces and the specimen itself is located opposite the stage surface, and
   a collection device, having at least one container for collecting a specimen that has been cut out wherein the collection device being conveyable to an open working space configured between the holder and the stage surface,
   wherein the first abutment surface includes an undercut portion and contacts, above the undercut portion, the specimen slide in a region below an upper edge of the specimen slide and higher than a point of contact of the spring element with the specimen slide.

8. A microscope comprising:
   an X-Y microscope stage and a holder, wherein the holder is arranged above a stage surface of said X-Y microscope stage and is adjustable in X and Y directions, for positioning a specimen slide,
   a baseplate being part of the holder and the specimen slide being arranged in an opening formed in the baseplate, wherein the opening has support surfaces and abutment surfaces for the specimen slide, and
   a spring element mounted on the base plate, so that a specimen arranged on the specimen slide is pressed against at least a first of the abutment surfaces and the specimen itself is located opposite the stage surface, wherein the first abutment surface includes an undercut portion and contacts, above the undercut portion, the specimen slide in a region below an upper edge of the specimen slide and higher than a point of contact of the spring element with the specimen slide.

* * * * *